(12) United States Patent
Pyayt et al.

(10) Patent No.: US 11,181,482 B1
(45) Date of Patent: Nov. 23, 2021

(54) MOBILE COLORIMETRIC ASSAY DEVICE

(71) Applicant: University of South Florida, Tampa, FL (US)

(72) Inventors: Anna Pyayt, Tampa, FL (US); Arsenii Zhdanov, Tampa, FL (US); Jordan Keefe, St. Petersburg, FL (US); Luis Franco-Waite, Lutz, FL (US)

(73) Assignee: University of South Florida, Tampa, FL (US)

( * ) Notice: Subject to any disclaimer, the term of this patent is extended or adjusted under 35 U.S.C. 154(b) by 578 days.

(21) Appl. No.: 16/121,932

(22) Filed: Sep. 5, 2018

Related U.S. Application Data

(60) Provisional application No. 62/566,884, filed on Oct. 2, 2017.

(51) Int. Cl.
| | | |
|---|---|---|
| G01N 21/78 | (2006.01) | |
| G01N 21/25 | (2006.01) | |
| G01N 21/64 | (2006.01) | |
| G01N 21/27 | (2006.01) | |
| G01N 33/543 | (2006.01) | |
| G01N 21/03 | (2006.01) | |
| G01N 21/29 | (2006.01) | |
| G01N 33/569 | (2006.01) | |
| G01N 33/574 | (2006.01) | |

(52) U.S. Cl.
CPC ......... *G01N 21/78* (2013.01); *G01N 21/0332* (2013.01); *G01N 21/253* (2013.01); *G01N 21/274* (2013.01); *G01N 21/29* (2013.01); *G01N 21/6452* (2013.01); *G01N 33/54386* (2013.01); *G01N 33/569* (2013.01); *G01N 33/574* (2013.01)

(58) Field of Classification Search
CPC .. G01N 21/78; G01N 21/0332; G01N 21/253; G01N 21/274; G01N 21/29; G01N 21/6452; G01N 33/54386; G01N 33/569; G01N 33/574
USPC ........................................ 435/7.92
See application file for complete search history.

(56) References Cited

U.S. PATENT DOCUMENTS

| | | | | |
|---|---|---|---|---|
| 5,863,742 A * | 1/1999 | Oh | ............. | C12Q 1/37 435/7.21 |
| 5,900,361 A * | 5/1999 | Klebe | ............. | G01N 1/2813 435/30 |
| 6,654,048 B1* | 11/2003 | Barrett-Lennard | ....... | G01J 3/52 348/180 |
| 2003/0170613 A1* | 9/2003 | Straus | ............. | C12Q 1/06 435/5 |
| 2012/0029408 A1* | 2/2012 | Beaudin | ............. | A61M 1/369 604/4.01 |
| 2012/0308990 A1* | 12/2012 | TerMaat | ............. | B01L 7/52 435/3 |
| 2014/0206412 A1* | 7/2014 | DeJohn | ............. | G01N 21/77 455/556.1 |
| 2014/0242612 A1* | 8/2014 | Wang | ............. | G01N 21/6452 435/7.23 |
| 2015/0152489 A1* | 6/2015 | Castro Signoret | ............. | G01N 33/54313 435/5 |
| 2017/0036208 A1* | 2/2017 | Veres | ............. | B01F 13/0059 |
| 2018/0030504 A1* | 2/2018 | Nolan | ............. | C12Q 2565/531 |
| 2018/0264464 A1* | 9/2018 | Greet | ............. | B01L 3/502715 |
| 2020/0393359 A1* | 12/2020 | Ozcan | ............. | G01N 33/49 |
| 2021/0147785 A1* | 5/2021 | Buzalewicz | ............. | C12M 41/48 |
| 2021/0230533 A1* | 7/2021 | Fan | ............. | G01N 33/56983 |

FOREIGN PATENT DOCUMENTS

WO 2013010178 A1 1/2013

OTHER PUBLICATIONS

Catalani, C. et al., 2013. mHealth for HIV Treatments Prevention: A Systematic Review of the Literature. The Open AIDS Journal 7, 17-41.
Stopinska-Gluszak, U. et al., 2006. Effect of estiogen/progesterone hormone replacement therapy on natural killer cell cytotoxicity and immunoregulatory cytokine release by peripheral blood mononuclear cells of postmenopausa women. Journal of Reproductive Immunology 69, 65-75.
17OH Progesterone ELISA for Routine Analysis, 2014. DiaMetra, DCM004-9, Ed. Jan. 2014 (pamphlet).
Abraham, G.E. et al., 1971. Simultaneous Measurement of Plasma Progesterone, 17-Hydroxyprogesterone & Estradiol-17B by Radioimmunoassay. Analytical Letters 4(6), 325-335.
Archibong, E. et al., Aug. 2016. A mobile phone-based approach to detection of hemolysis. Biosensors and Bioelectronics 88, 204-209.
Barbagallo, M. et al., 2001. Vascular Effects of Progesterone: Role of Cellular Calcium Regulation. Hypertension 37, 142-147.

(Continued)

*Primary Examiner* — Ann Y Lam
(74) *Attorney, Agent, or Firm* — Smith & Hopen, P.A.; Michele L. Lawson

(57) ABSTRACT

A mobile phone-based system for ELISA (MELISA). The MELISA system can perform all steps of ELISA procedure and output hormone concentration values. The system includes a heater that keeps the temperature required for sample incubation, illumination system for sample image capturing, and a digital camera system. All components are enclosed in a dark box to create optimal light conditions for image capturing. After sample images are captured, they are digitally processed, and hormone concentration values are reported based on colorimetric data from the samples. The system can be used to complete all steps of the assay, including incubation and reading. It is lightweight, can be fabricated at low cost, is portable, and can transfer test results via mobile phone. MELISA can be calibrated for accurate measurements of progesterone and has demonstrated successful measurements with the calibrated system.

17 Claims, 11 Drawing Sheets

(56) References Cited

OTHER PUBLICATIONS

Brown, G., 2000. How Autofocus Cameras Work [WWW Document]. HowStuffWorks.

Catalani, C. et al., 2013. mHealth for HIV Treatment & Prevention: A Systematic Review of the Literature. The Open AIDS Journal 7, 17-41.

Cheemalapati, S. et al., 2016. Dynamic visualization of photothermal heating by gold nanocages using thermoresponsive elastin like polypeptides. Nanoscale 8, 18912-18920.

Cheng, C. et al., Jul. 2013. iACT—An interactive mHealth monitoring system to enhance psychotherapy for adolescents with sickle cell disease. 2013 35th Annual International Conference of the IEEE Engineering in Medicine and Biology Society (EMBS), 2279-2282.

Csapo, A.I. et al., Jan. 1974. Progesterone Deficiency and Premature Labour. British Medical Journal 1, 137-140.

Elder, P.A. et al., 1987. An enzyme-linked immunosorbent assay (ELISA) for plasma progesterone: immobilised antigen approach. Clinica Chimica Acta 162, 199-206.

Hsu, E. et al., Aug. 2008. Light mixture estimation for spatially varying white balance. ACM Transactions on Graphics, vol. 27, No. 3, Article 70.

Inder, W.J. et al., 2012. Measurement of salivary cortisol in 2012—laboratory techniques and clinical indications. Clinical Endocrinology 77, 645-651.

Jenkins, C. et al., 2016. Stroke patients and their attitudes toward mHealth monitoring to support blood pressure control and medication adherence. mHealth 2:24, 7 pages.

Katz, R. et al., May 2012. Lessons From a Community-Based mHealth Diabetes Self-Management Program: "It's Not Just About the Cell Phone". Journal of Health Communication 17, 67-72.

Kim, J.J. et al., Feb. 2013. Progesterone Action in Endometrial Cancer, Endometriosis, Uterine Fibroids, and Breast Cancer. Endocrine Reviews 34(1), 130-162.

Konnaiyan, K.R. et al., 2016. mHealth dipstick analyzer for monitoring of pregnancy complications. 2016 IEEE Sensors.

Konnaiyan, K.R., Oct. 2015. Smartphone Based 3D Printed Colorimeter For Biomedical Applications (thesis).

McGeough, C.M. et al., Oct. 2013. Camera Phone-Based Quantitative Analysis of C-Reactive Protein ELISA. IEEE Transactions on Biomedical Circuits and Systems 7(5), 655-659.

Zhdanov, A. et al., 2018. Mobile phone based ELISA (MELISA). Biosensors and Bioelectronics 103, 138-142.

Stopinska-Gluszak, U. et al., 2006. Effect of estrogen/progesterone hormone replacement therapy on natural killer cell cytotoxicity and immunoregulatory cytokine release by peripheral blood mononuclear cells of postmenopausal women. Journal of Reproductive Immunology 69, 65-75.

Turner-McGrievy, G.M. et al., 2013. Comparison of traditional versus mobile app self-monitoring of physical activity and dietary intake among overweight adults participating in an mHealth weight loss program. Journal of the American Medical Informatics Association 20, 513-518.

Vashist, S.K. et al., 2015. A smartphone-based colorimetric reader for bioanalytical applications using the screen-based bottom illumination provided by gadgets. Biosensors and Bioelectronics 67, 248-255.

Xu, B. et al., Jun. 2012. Serum progesterone level effects on the outcome of in vitro fertilization in patients with different ovarian response: an analysis of more than 10,000 cycles. Fertility and Sterility 97:6, 1321-1327.

Yoshimi, T. et al., 1968. The measurement of plasma progesterone. Steroids 11(4), 527-540.

Zangheri, M. et al., 2015. A simple and compact smartphone accessory for quantitative chemiluminescence-based lateral flow immunoassay for salivary cortisol detection. Biosensors and Bioelectronics 64, 63-68.

\* cited by examiner

MOBILE COLORIMETRIC ASSAY DEVICE

CROSS-REFERENCE TO RELATED APPLICATIONS

This nonprovisional application claims priority to U.S. Provisional Patent Application No. 62/566,884, entitled "Mobile Phone-Based Elisa (MELISA)," filed Oct. 2, 2017 by the same inventors, which is incorporated herein by this reference.

GOVERNMENT SUPPORT

This invention was made with government support 1701081 awarded by the National Science Foundation. The Government has certain rights in the invention.

TECHNICAL FIELD

Embodiments of this disclosure relate, generally, to computer-effectuated biotesting.

More specifically, embodiments relate to mobile phone-based enzyme-linked immunosorbent assays.

BACKGROUND

Enzyme-linked immunosorbent assay (ELISA) is one of the most important technologies for biochemical analysis critical for diagnosis and monitoring of many diseases and disorders. Traditional systems for ELISA incubation and reading are expensive and bulky, thus cannot be used at point-of-care or in the field.

For example, cancer detection and treatment are important aspects of the practice of modern medicine. In particular, ovarian cancer is the fifth leading cause of all cancer related mortality among women. Since ovarian cancer is asymptomatic at early stages, most patients present with advanced disease (such as stage III or stage IV) when diagnosed. Despite radical surgery and chemotherapy, the five-year survival rate of ovarian cancer at stages III and IV is only 33% compared to 90% at stage I. This statistic alone highlights the need for early diagnosis and large-scale screening, at least among high-risk populations. However, existing diagnosis methods such as biopsy, medical imaging, and genetic analysis cannot be used frequently for routine screening, and oftentimes lengthy and complex testing procedures associated with these methods hinder high-risk populations from seeking immediate medical care. Thus, the lack of cost-effective methods that can achieve frequent, simple and non-invasive testing hinders early detection and renders high mortality in ovarian cancer patients.

Annual transvaginal sonography has been used to screen for ovarian cancer among subjects with a family history of ovarian cancer, which has shown limited efficacy when the ovarian volume remains normal. Another common screening method is a serum CA125 test, an enzyme-linked immunosorbent assay (ELISA) with a sensitivity of 72% at specificity 95%. The sonography and serum screening methods are invasive, costly, and provide results that are instrument dependent and, as a result, they cannot be reasonably established at point-of-care (POC) settings.

POC diagnostics are appealing in terms of disease monitoring and control, including infectious diseases, cancer and diabetes, in both resource-limited and resource-rich settings. To offer POC testing by the bedside, the World Health Organization (WHO) has expressed the need for inexpensive, disposable, and easy-to-use diagnostic devices, for example for resource-limited settings where there are limitations with trained personnel, infrastructure, and medical instruments. Features of such devices should include functionality under high humidity and temperature, and robust operation in the absence of reliable electricity and water supply. The need for such devices also extends to resource-rich settings such as airports, community clinics, and emergency rooms, where frequent testing and rapid results are needed, or access to central laboratories may be limited (for example, for blood sugar testing or influenza screening).

With advances in microelectromechanical systems (MEMS), miniaturization of ELISA on a single microchip has become feasible. Microchip ELISA results can be seen by the naked eye; however, analyte concentrations cannot be quantitatively measured using this method. Quantitative detection technologies such as fluorescence detection, chemiluminescence or electrical detection are expensive, technologically complex, and require bulky detection setups. For instance, fluorescence or chemiluminescence detection often requires the use of a charge-coupled device (CCD) camera interfaced with an expensive fluorescence microscope. Electrical detection of microchip ELISA requires a reliable power supply and delicate circuitry to measure the change in impedance induced by the analyte. Colorimetric detection of on-chip ELISA requires a CCD camera coupled to a microscope and connected to a computer with an analysis program. Thus, all of these solutions require a laboratory environment to be utilized. Thus, despite the widespread need, current state-of-the-art diagnostic technologies such as polymerase chain reaction (PCR), ELISA, or microarray have practical challenges hindering them from being established at the POC. Simply, as described above, these detection methods are not ideal for POC testing despite the use of miniaturized microchips and, thus, have not been adopted in for POC applications.

Recently, mobile phones have become a popular platform for point-of-care testing. The term mHealth has been adopted by the World Health Organization to cover medical services and practices that utilize mobile phones or other portable electronics. For example, pregnancy complication monitoring can be done on a mobile phone (Archibong et al., 2017; Konnaiyan et al., 2016). Stroke patients can now monitor their blood pressure with a mobile phone application (Jenkins et al., 2016). Other applications are currently being developed for diabetic patients (Katz et al., 2012), weight control (Turner-Mcgrievy et al., 2013), patients with sickle cell disease (Cheng et al., 2013), etc. Additionally, mobile platforms can be used for HIV prevention, care, and treatment (Catalani et al., 2013). Mobile phones are already widely available across the globe, including low and middle-income countries. Contemporary cellphones have several built-in sensors including: cameras, light-sensors, microphones, etc. Availability of the aforementioned sensors integrated into a convenient mobile platform has enabled a number of mobile phone based diagnostic systems.

One of the popular biomedical testing technologies that would be very beneficial to translate to a mobile platform is ELISA. However, up to date, most of the research was focused on using a phone camera as a read-out, while there is no complete system that allows conducting all of the steps of the ELISA protocol (McGeoug and O'Driscoll, 2013; Vashist et al., 2015). Studies related to point-of-care hormone measurement are very limited and mostly focus on cortisol detection (Zangheri et al., 2015). Patent publication WO/2013010178 to Wang et al. discloses a mobile device that is capable of imaging a microchip ELISA result. However, the device and system disclosed in Wang does not teach the ELISA incubation in conjunction with imaging and processing the results all in one device.

Accordingly, what is needed is an all in one mobile phone-based device that simplifies and reduces the cost of current ELISA procedures, for example for measurement of progesterone in whole blood samples. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY

This summary is provided to introduce a selection of concepts in a simplified form. These concepts are described in further detail in the detailed description of example embodiments of the disclosure below. This summary is not intended to identify key features or essential features of the claimed subject matter, nor is it intended to be used to limit the scope of the claimed subject matter.

Embodiments disclosed herein include a system for measuring the concentration of a target binding domain in a biological sample from a subject, the system comprising: a housing comprising a top, a bottom, a first side, a second side, a front, and a rear; an aperture disposed on the top of the housing; wherein the housing further comprises two compartments, an inner chamber and an outer chamber; wherein the aperture disposed on the top of the housing opens into the inner chamber; wherein the front of the housing has a door configured to move between an open configuration and a closed configuration, wherein the closed configuration minimizes external light entering the housing; a thermally conductive sample holder comprising a sample holder tray and a heating element within a water bath; wherein the inner chamber is configured to hold the thermally conductive sample holder; wherein the sample holder tray has a plurality of apertures for receiving enzyme-linked immunosorbent assay (ELISA) microwells, such that a portion of the microwells are submerged partially within the water bath; a light source in the inner chamber disposed under the sample holder tray; and circuitry and relays for controlling the system disposed in the outer chamber. For example, in accordance with one embodiment, A system for measuring the concentration of a target binding domain in a biological sample from a subject, wherein the aperture disposed on the top of the housing is configured to receive a mobile device, wherein the mobile device camera is positioned above the aperture.

A system for measuring the concentration of a target binding domain in a biological sample from a subject, wherein the mobile device camera acquires color images of the ELISA microwells disposed within the inner chamber of the housing.

A system for measuring the concentration of a target binding domain in a biological sample from a subject, wherein the color images are analyzed by an application in the mobile device to determine the color intensity data of at least a selected portion of the color image.

A system for measuring the concentration of a target binding domain in a biological sample from a subject, wherein the application uses a baseline curve calculation to normalize the color intensity data.

A system for measuring the concentration of a target binding domain in a biological sample from a subject, wherein the mobile device can correlate the color intensity data with the concentration of the target binding domain in the biological sample.

A system for measuring the concentration of a target binding domain in a biological sample from a subject, wherein the mobile device correlates the color intensity data with demographic data from the subject.

A system for measuring the concentration of a target binding domain in a biological sample from a subject, wherein the application generates a report regarding the concentration of the target binding domain in the biological sample.

A system for measuring the concentration of a target binding domain in a biological sample from a subject, wherein the report indicates at least one of a presence or absence of a predetermined pathological condition.

A system for measuring the concentration of a target binding domain in a biological sample from a subject, wherein the color image of the ELISA microwells is analyzed to determine the color in intensity by comparing pixel values to a predetermined threshold to determine the color pixel values of a selected portion of the color image.

A system for measuring the concentration of a target binding domain in a biological sample from a subject, wherein the color pixel values are compared to color pixel values of a background portion of the color image to a predetermined color intensity of a background portion of a calibration image to normalize the color intensity based on the comparison.

A system for measuring the concentration of a target binding domain in a biological sample from a subject, wherein the predetermined pathological condition comprises one of cancer, human immunodeficiency virus, kidney injury, brain injury, and peritonitis.

A system for measuring the concentration of a target binding domain in a biological sample from a subject, wherein the target binding domain is one of CD4 cells, neutrophils, kidney injury molecule 1 biomarker, a brain-derived neurotrophic factor biomarker, a cancer antigen 125 biomarker, and $E.\ coli$.

A system for measuring the concentration of a target binding domain in a biological sample from a subject, wherein the circuitry and relays for controlling the system disposed in the outer chamber comprises an Arduino Mega 2560 microcontroller which measures and controls the temperature of the system.

A system for measuring the concentration of a target binding domain in a biological sample from a subject, wherein the mobile device is one of a cell phone with built-in camera and a tablet having access to a remote computer.

In further embodiments, a method for analyzing a target binding domain in a biological sample, the method comprising: providing a biological sample from a subject; loading the biological sample into a tray comprising microwells configured to perform an enzyme-linked immunosorbent assay (ELISA) specific to the target binding domain; loading the tray into a housing device; closing the housing device; performing the ELISA; generating a color image of the tray using a mobile device positioned over an aperture on the top of the housing device; determining the color intensity of a selected portion of the color image; correlating the color intensity of the selected portion of the color image with a target binding domain concentration using a baseline curve calculation; and reporting the concentration of the target binding domain.

A method for analyzing a target binding domain in a biological sample, wherein the housing device comprises: a top, a bottom, a first side, a second side, a front, and a rear; the aperture disposed on the top of the housing; wherein the housing further comprises two compartments, an inner chamber and an outer chamber; wherein the aperture disposed on the top of the housing opens into the inner chamber; wherein the front of the housing has a door configured to move between an open configuration and a closed configuration, wherein the closed configuration minimizes external light entering the housing; a thermally conductive sample holder comprising a sample holder tray and a heating element within a water bath; wherein the inner chamber is configured to hold the thermally conductive sample holder; wherein the sample holder tray has a plurality of apertures for receiving enzyme-linked immunosorbent assay (ELISA) microwells, such that a portion of the microwells are submerged partially within the water bath; a light source in the inner chamber disposed under the sample holder tray; and circuitry and relays for controlling the system disposed in the outer chamber.

A method for analyzing a target binding domain in a biological sample, wherein the report of the concentration of a target binding domain includes displaying the concentration of a target binding domain on the mobile device.

A method for analyzing a target binding domain in a biological sample, wherein the report of the concentration of the target binding domain comparison the concentration to a threshold concentration and reporting one of a positive physiological condition result and a negative physiological condition result based on the comparison.

A method for analyzing a target binding domain in a biological sample, wherein correlating the color intensity of the selected portion of the color image with a target binding domain concentration using a baseline curve calculation is performed by determining color pixel values of a selected portion of the color image and comparing to a baseline curve calculation; and further comprising normalizing the color intensity of the color image by comparing the color intensity of a background portion of the color image to a color intensity of a background portion of a calibration image.

In a further embodiment, a kit for performing an ELISA, wherein the housing device comprises: a top, a bottom, a first side, a second side, a front, and a rear; the aperture disposed on the top of the housing; wherein the housing further comprises two compartments, an inner chamber and an outer chamber; wherein the aperture disposed on the top of the housing opens into the inner chamber; wherein the front of the housing has a door configured to move between an open configuration and a closed configuration, wherein the closed configuration minimizes external light entering the housing; a thermally conductive sample holder comprising a sample holder tray and a heating element within a water bath; wherein the inner chamber is configured to hold the thermally conductive sample holder; wherein the sample holder tray has a plurality of apertures for receiving enzyme-linked immunosorbent assay (ELISA) microwells, such that a portion of the microwells are submerged partially within the water bath; a light source in the inner chamber disposed under the sample holder tray; and circuitry and relays for controlling the system disposed in the outer chamber.

BRIEF DESCRIPTION OF THE DRAWINGS

For a fuller understanding of the invention, reference should be made to the following detailed description, taken in connection with the accompanying drawings, in which.

DETAILED DESCRIPTION

Figure 1A:
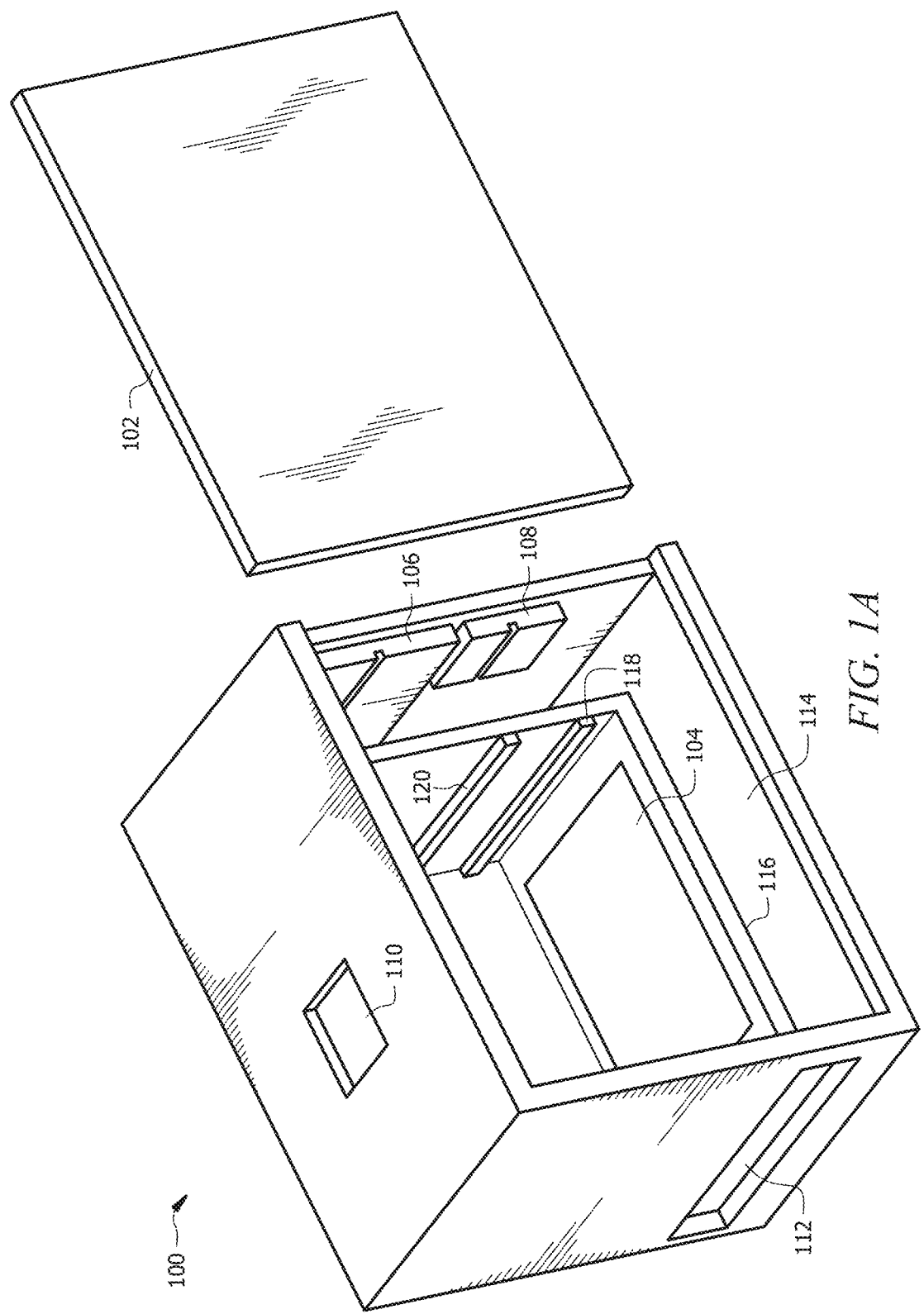
FIG. 1A-1B depict a 3D model of the system, according to an embodiment of the claimed subject matter.

In the following detailed description, reference is made to the accompanying drawings, which form a part thereof, and within which are shown by way of illustration specific embodiments by which the claimed subject matter may be practiced. It is to be understood that other embodiments may be utilized, and structural changes may be made without departing from the scope of the claimed subject matter. These embodiments are described in sufficient detail to enable those of ordinary skill in the art to practice the claimed subject matter, and it is to be understood that other embodiments may be utilized, and that structural, logical, and electrical changes may be made within the scope of the disclosure.

From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. Only those process acts and structures necessary to understand the embodiments of the disclosure are described in detail below. A person of ordinary skill in the art will understand that some process components are inherently disclosed herein and that adding various conventional process components and acts would be in accord with the disclosure. In this description, specific implementations are shown and described only as examples and should not be construed as the only way to implement the present disclosure unless specified otherwise herein.

Illustrations presented herein are not meant to be actual views of any particular material, component, or system, but are merely idealized representations that are employed to describe embodiments of the disclosure. Referring in general to the following description and accompanying drawings, various embodiments of the present disclosure are illustrated to show its structure and method of operation. Common elements of the illustrated embodiments may be designated with similar reference numerals. It should be understood that the figures presented are not meant to be illustrative of actual views of any particular portion of the actual structure or method but are merely idealized representations employed to more clearly and fully depict the claimed subject matter.

Any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

Any headings used herein should not be considered to limit the scope of embodiments of the invention as defined by the claims below and their legal equivalents. Concepts described in any specific heading are generally applicable in other sections throughout the entire specification.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, "about" means approximately or nearly and in the context of a numerical value or range set forth means±15% of the numerical. In an embodiment, the term "about" can include traditional rounding according to significant figures of the numerical value. In addition, the phrase "about 'x' to 'y'" includes "about 'x' to about 'y'".

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as agents which are effective for producing an intended result. Compositions according to the instant application may be used to effect a favorable change in the underlying condition, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated.

As used herein, the term "target binding domain," is interchangeable with any of "biomolecule," "antigen," or "pathogen" and includes whole cells, viruses, and bacteria. As used herein, the term "target binding domain" is meant to include any domain on which another molecule (e.g., an antibody) may bind in a chemical assay.

While embodiments of this disclosure discuss the use of an ELISA, the claimed subject matter could be used with any assay that produces a visual result or a result that can be captured on a camera. Any assay that tests for the presence of enzymes, specific compounds, antibodies, hormones, or an analyte which produces a visual result may be practiced with the claimed subject matter (e.g., absorbance and colorimetric assays). Nonlimiting examples of different assays which one of skill in the relevant art would understand could be practiced with the current disclosure include: 660 nm protein assay; BCA assay; Bradford Assay; Modified Lowry; Colorimetric Peptide Assay; Fluorometric Peptide Assay; Bicinchoninic Acid Assay; para-Nitrophenylphosphate assay; Malachite Green Assay; or any assay that uses chromogenic substrates (e.g., BCIP, DAB, 4CN, and Fast Red).

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the user or practitioner when the device is in use by the user or practitioner. The distal end is the end opposite the proximal end, along the longitudinal direction of the device, or the end furthest from the user or practitioner.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Generally, in certain embodiment, the claimed subject matter is a complete low-cost mobile phone-based system that allows execution of all of the Enzyme-linked immunosorbent assay (ELISA) steps without any additional equipment. (Zhdanov, Arsenii, et al., *Mobile phone based ELISA (MELISA)*, Biosensors and Bioelectronics 103 (2018) 138-142). This system can be used to complete all steps of the assay, including incubation and reading. It weighs just one pound, can be fabricated at low cost, portable, and can transfer test results via mobile phone. Its successful application to hormone measurements is demonstrated herein as a system focused on measurement of hormone levels. Other suitable applications of the system are contemplated herein as well. The components of the MELISA system include an enclosure/housing, a water bath heater, a light source, and an Arduino microcontroller. The mobile phone platform also permits image processing and sample concentration assessment using a custom algorithm. The image processing algorithm can be adjusted for a variety of colorimetric applications.

An embodiment of the MELISA system provides a system and method for detecting microchip ELISA results using a mobile device with an imaging apparatus to measure a biomarker, cell, or pathogen (e.g., virus or bacteria) concentration in a sample. The mobile device may have an integrated mobile application or a lens less charge-coupled device connected to an additional device with an integrated application to facilitate the MELISA system. A sample is loaded onto a microchip system configured to provide colorimetric biomarker feedback. The colormetric feedback is imaged by the mobile device and analyzed using the mobile device, either directly using the processing systems of the mobile device or through communication with a remote processing system using the communications systems of the mobile device to provide results.

An embodiment of the MELISA system provides for testing of a biomarker indicative of a predetermined pathological condition. The system includes an ELISA system configured to receive the biological sample from a subject and provide colorimetric biomarker feedback indicative of a testing related to the predetermined pathological condition. The image processing device, which may be a mobile phone, is configured to correlate the color intensity of at least a selected portion of the color image with a biomarker concentration and generate a report regarding the concentration of the biomarker concentration.

An embodiment of the MELISA system provides for a method to determine color intensity of a selected portion of a colormetric ELISA correlating the color intensity with the concentration of the test target binding domain, antigen, pathogen, or biomarker using a baseline curve calculation, and reporting the concentration of the target binding domain, antigen, pathogen, or biomarker.

An embodiment of the MELISA system provides for each part of the system to be broken down to its constituent parts to enable easy transport and subsequent reassembly. The system is such that with a set of instructions an end user could reassemble the system to provide point of care ELISA regardless of additional resources, such as in a remote location.

An embodiment of the MELISA system provides for an application which can be loaded onto either a mobile phone or computer to receive the colormetric ELISA image and provide detailed results, enabling immediate data processing of the results without the need for any peripheral equipment. The application can differentiate the color intensity developed on the ELISA tray after it has been incubated in the same device, correlate the color intensity with a concentration of the target biomarker in the sample, and report or display the concentration of the target biomarker or correlate the results to a predetermined condition, such as the presence or absence of neoplastic cells, or a pathogen.

An embodiment of the MELISA system provides for standardized lighting source to image the ELISA during or after incubation as well as a standardized distance between the tray in which the ELISA is performed and the mobile device or camera mounted on top of the device. The device will also block any outside ambient light from interfering with the imaging by closing the device off from any external light sources. In one embodiment the light source can be light emitting diodes (LEDs), which may be white LEDs, and power source for the LEDs.

An embodiment of the MELISA system provides for a device with two enclosures, where at least one enclosure is configured to incubate the ELISA and block out external light, and the other enclosure is configured to contain additional support devices such as batteries and a light source. The dual enclosure further provides an advantage by permitting the ELISA enclosure to remain separate from the other enclosure to facilitate any maintenance to the device while not disturbing either the incubation of the ELISA or the data collection of the images of the ELISA. Further, by utilizing a two enclosure design the device provides for additional protection from external heat or light sources which may interfere with aspects of the ELISA incubation or data collection. The internal enclosure designed to incubate the assay also provides for a fixed stable position for the assay tray to enable easy positioning to gather data either during or after incubation.

An embodiment of the MELISA system provides for multiple internal enclosures within the device to allow for multiple ELISA incubations to run concurrently. In some embodiments there are different heating sources for each of these internal compartments to allow for differential heating of the different assays all within the same device. There are various applications for a system that allows for multiple assays to run simultaneously including comparison ELISA from either the same subject or multiple subjects.

An embodiment of the MELISA system provides for one enclosure which can incubate the ELISA assay as well as containing the support devices to facilitate both incubation and data collection.

An embodiment of the MELISA system provides for heating sensors to facilitate the incubation of the assay in a controlled environment which controls, and sensor readouts positioned on the outside of the device to enable an end users control.

An embodiment of the MELISA system provides for a kit which contains every component of the system packaged with instructions to assemble the device and perform the assays with or without external power supplies. The embodiment provides for the method of assembling the system and performing the assay to test for a biomarker or pathogen in a sample from a subject. In some embodiments the MELISA system has a mobile device or other additional devices connected either wired or wirelessly (e.g., Bluetooth® or Wi-Fi).

An embodiment of the MELISA in which the biological sample is loaded onto a plastic tray for ELISA assay and loaded into an inner chamber in the MELISA system apparatus to initiate incubation, the ELISA assay is then processed, and data collected during incubation and when incubation is complete. The image with the colormetric data is then processed in the mobile device or computer to provide analysis and results. This method and system can utilize ELISA types, nonlimited examples of which include direct ELISA, indirect ELISA, sandwich ELISA, and competitive ELISA. Furthermore, multiple biomarkers may be tested simultaneously on the same ELISA tray (e.g., in different microchannels). In some implementation, polymethyl-methacrylate (PMMA) microfluidic chips are used.

In some embodiments the MELISA system can control multiple incubation cycles depending on the types of reagents used in the system. The MELISA system is able gather colormetric data at any point during incubation or between incubation cycles.

In some embodiments the MELISA system can be used as a diagnostic tool in medicine and plant pathology, as well as quality-control check in various industries.

Performing an ELISA involves at least one antibody with specificity for a particular antigen. The sample with an unknown amount of antigen is immobilized on a solid support (usually a polystyrene microtiter tray) either non-specifically (via adsorption to the surface) or specifically (via capture by another antibody specific to the same antigen, in a sandwich ELISA). After the antigen is immobilized, the detection antibody is added, forming a complex with the antigen. The detection antibody can be covalently linked to an enzyme or can itself be detected by a secondary antibody that is linked to an enzyme through bioconjugation. Between each step, the tray is typically washed with a mild detergent solution to remove any proteins or antibodies that are non-specifically bound. In some embodiments, the MELISA system is configured to facilitate washing steps without opening the inner compartment. In some embodiments, the MELISA system is configured to facilitate washing steps by opening the inner compartment. After the final wash step, the plate is developed by adding an enzymatic substrate to produce a visible signal, which indicates the quantity of antigen in the sample.

In some embodiments of the MELISA system image analysis and color intensity correlation can be performed by an application stored on and executed by a process of the mobile device, such as an integrated mobile application or any additional connected device such as a computer wirelessly connected utilizing an image processing software application. The images may also be transmitted to any other device which may contain medical records or data for comparison to the recorded colorimetric data and analysis and color intensity correlation.

The software application run on either the mobile device or external computer may process the selected image of the ELISA color intensity determining "detection regions" within the image that represent the amount of antigen in the sample. In addition, the application may store previous images which can then be compared to any new images taken. In this way, the application may provide real time intensity changes in a biological sample.

The software application uses color intensity of the image pixel values as red, green, and blue pixel values using an RGB color model, in which red, green, and blue pixel values vary from 0 to 255. When the pixel value is at 255, the color signal is saturated. In addition, in some embodiments, blue pixel values, green pixel values, red pixel values, or other wavelengths can be used for colorimetric image intensity data collection or for any other analysis.

In some instances, imaged ELISA tray regions may have a low color intensity and do not illustrate clear difference from the background of the image. To facilitate region selection by the mobile application, some images maybe modified to add markers or indicators next to the imaged ELISA tray to assist the selection of the detection regions. In addition, markers can be physically placed on the ELISA tray to facilitate detection region recognition during image analysis. In some instances, the mobile application assumes that the captured images are oriented horizontally with small rotation angles. As such, assumptions can be made that the detection regions are axis-aligned and each region in the same image is vertically aligned.

To minimize the illumination difference between analyzed images, the color intensity can be normalized based on the difference in the backgrounds (specifically, regions excluding the detection regions) between one or more stored calibration images ("baseline images") and the sample image. The application selects a typical background region from the sample image and compares the R values therein to an average of R values from the background regions of the calibration images. The R values from the selected region in sample image is then offset, or normalized, by deducing the R value difference. In some instances, microchips can include a separate calibration well in the ELISA tray and relative R values can be determined from the calibration well and the other wells in the ELISA tray for normalization. The application then applies an average of the normalized R values from the detection region against a baseline curve relating R values to analyte concentrations. The baseline curve is calculated by determining a regression line correlating R values of the calibration images to known analyte concentrations of the calibration images. In addition, the application can receive new calibration images to recalibrate the baseline curve at any time (for example, by calculating R values of the new images and updating baseline curve regression parameters).

The application may also compare the analyte concentration to a threshold concentration to determine if the analyte concentration is above the threshold concentration, indicating a positive (or preliminary positive) result, or if the analyte concentration is below the threshold concentration, indicating a negative (or preliminary negative) result. The application can then also display the positive/negative result on the mobile device screen. In addition, the application can receive demographic or epidemiologic variables (for example through message texting and data sharing via mobile networks or through direct user input into the mobile device) and use such variables to facilitate diagnosis. In one example, malignancy prediction can incorporate menopausal status as a variable.

The integrated mobile application can be employed in both resource-rich and resource-limited settings because of increasingly available mobile networks, where the appropriate clinical information can be instantly and remotely transferred between patients and physicians. This can allow remote patient diagnosis and instructing. In one non-limited example, a patent can perform the method of the MELISA system, sends the sample images or the application analysis or report to a medical practitioner who then can instruct the patient regarding the results. The results can be used to adjust medication, make decisions to start treatments or medications, make decisions to stop or adjust treatments, or establish the need for a follow-up appointment with the medical practitioner. In addition, the methods and devices associated with the MELISA system can be broadly applied as a biotechnological tool for any disease having a reasonably well-described ELISA biomarker in biological samples from a subject. Non-limited examples of what the sample can be include urine, plasma, whole blood, serum, or saliva.

In some embodiments the MELISA uses ELISA-based p24 antigen detection (for example, from plasma) or CD4 cell count detection for detecting HIV, ELISA-based KIM-1 detection or NGAL (neutrophil gelatinase-associated lipocalin) detection (for example, from urine) for detecting kidney injury, or ELISA-based BDNF (brain-derived neurotrophic factor) detection for detecting traumatic brain injury. The above methods can also be applied to ELISA-based *E. coli* detection, for example from whole blood samples. In some cases, multiple analytes can be detected on the same ELISA. For example, urine HE4 and serum CA125 can both be tested simultaneously on a single chip to assist in cancer detection. It is noted that, for purposes of this disclosure, the term biomarker may encompass proteins, cells, pathogens, etc.

In some embodiments the outer chamber is configured to contain pumps and gating devices to deliver reaction components in a temporal and spatial manner necessary to perform the ELISA in the inner chamber of the MELISA system. The inner chamber may also be configured with a device to agitate the ELISA tray to improve the incubation of the ELISA. This agitator may also be coupled to the light source in the inner chamber. The pumps and gating devices may be controlled by control devices mounted to the outer chamber or may be controlled by the mobile device.

Some embodiments of the MELISA system may include a chamber-based microchip design, considered a "micro-a-fluidic" approach. This design does not involve precise fluid flow and thus significantly facilitates automation of complicated biological reactions (such as ELISA, or alternatively, polymerase chain reaction (PCR) testing). The micro-a-fluidic ELISA of the MELISA system elicits a substantially high sensitivity (less than 10 picograms/milliliter, pg/ml), which is about two-to four-fold higher than the sensitivity of conventional microplate ELISA. In addition, assay time using the micro-a-fluidic approach can be reduced to about 10 minutes, in comparison to 4-6 hours for conventional ELISA. It is noted that this assay time can be varied greatly and even further reduced, for example in the range of two to three minutes or down to ten seconds, based on reagent capabilities and other factors. In addition, the micro-a-fluidic ELISA can potentially be fully automated to improve efficiency in the use of the system. Detection of micro-a-fluidic ELISA results can be achieved through conventional techniques or through a mobile device.

Figure 1B:
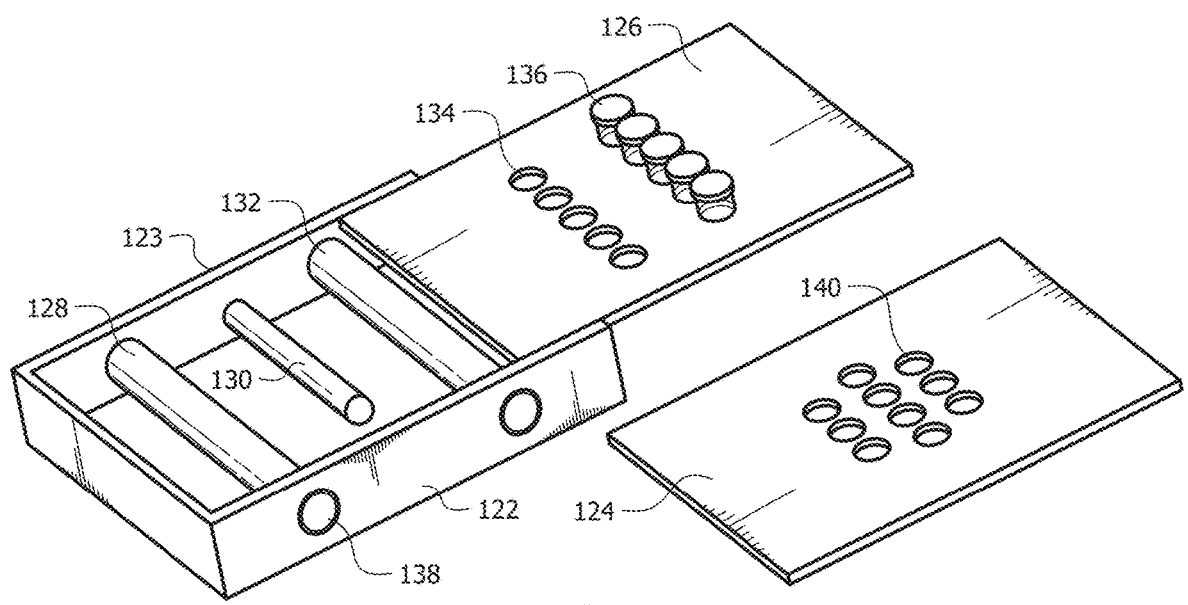

An embodiment of the MELISA system is shown in FIG. 1. The device housing 100 is comprised of two separate chambers or sections. The inner chamber 116 or section of the housing is the site where ELISA procedure steps take place, including incubation and image capture. A backlight LCD screen 104 is in the bottom of this inner chamber 116. The outer chamber 114 or section of the housing 100 is used to store the control circuitry 106 necessary for device operation. The control circuitry includes: an Arduino Mega 2560 microcontroller, two DC solid state relays 108, and an input/output (I/O) circuit for the microcontroller. A door 102 is designed to block out any light from outside sources and connects to the box by sliding into grooves. The plastic components were designed in Autodesk Inventor and the housing was 3D-printed in polylactic acid (PLA) plastic.

The housing 100 comprises an aperture 110 configured to allow a mobile device (not depicted) to take photographs of the ELISA results in inner chamber 116. The inner chamber 116 has guide rails 120 and 118 to facilitate insertion of the water bath 122 and heating tray 126. The outer chamber 114 is configured to include an opening 112 to allow cables and wires to run from inside to housing 100 when the housing door 102 is closed.

The device has two inserts—one for sample heating and the other for image capturing. The water bath 122 heater inserts were also designed in Autodesk Inventor but 3D-printed using acrylonitrile butadiene styrene (ABS) plastic rather than PLA because of better resistance of this material to higher temperatures. The heating tray 126 has holders 134 for the ELISA microwells 136 arranged in two lines of five, equidistant from two copper tubes 128 and 132 with inserted heating elements. The copper tubes 128 and 132 extend out 138 of the water bath 122. The water bath 122 slides into the 3D-printed housing 100 with the heating elements and temperature sensor 130 connecting to the Arduino microcontroller, as well as a power supply. The image capturing tray 124 has ELISA microwell holders 140 arranged in a hexagonal pattern for optimal light distribution. The system is modular, enabling custom modifications of the whole system.

Incubator Design

Figure 2A:
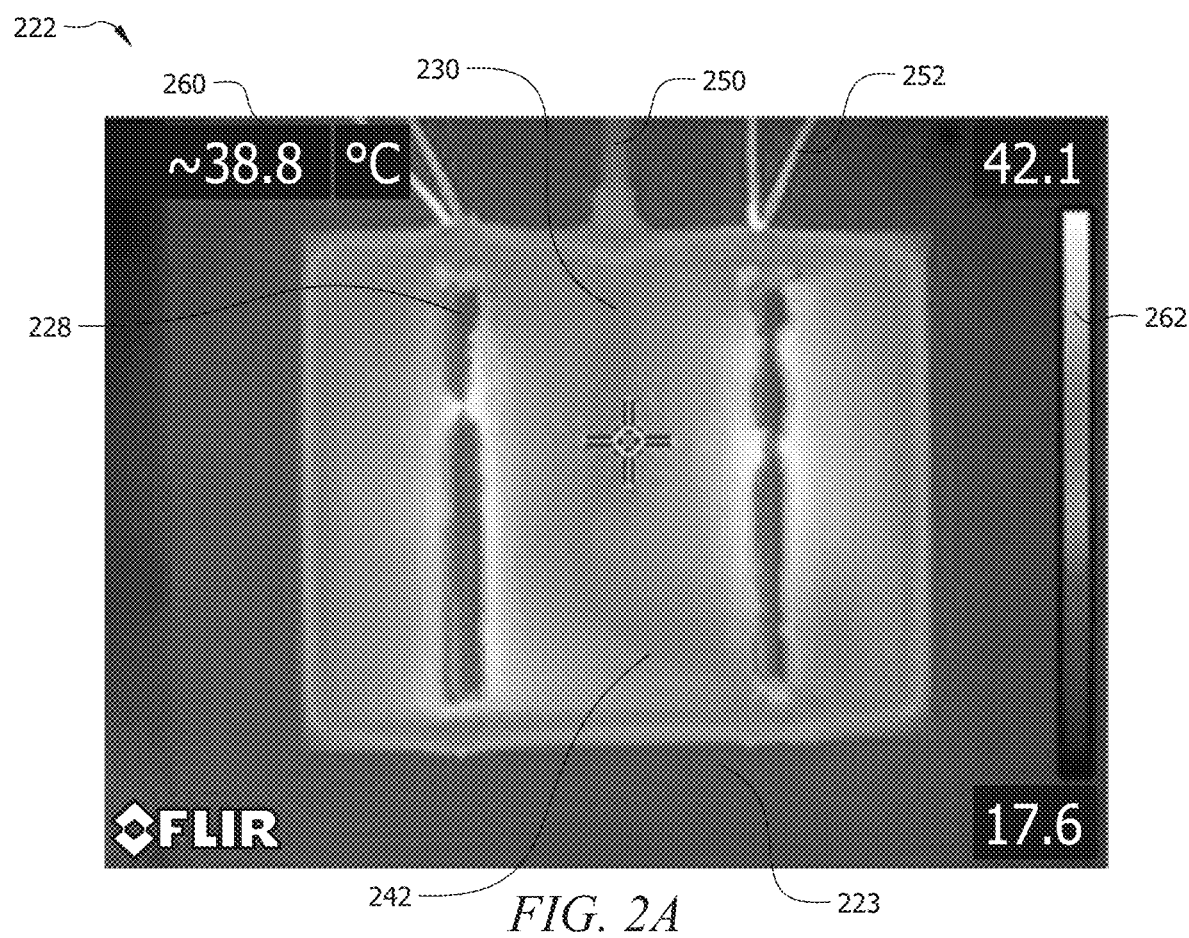
FIGS. 2A-2D depicts thermal characteristics of the water bath. 2A: Infrared thermal image (top view); 2B: Real image (top view); 2C: COMSOL simulation of heat distribution (side view); 2D: Water bath thermodynamic tuning curve.
Figure 2B:
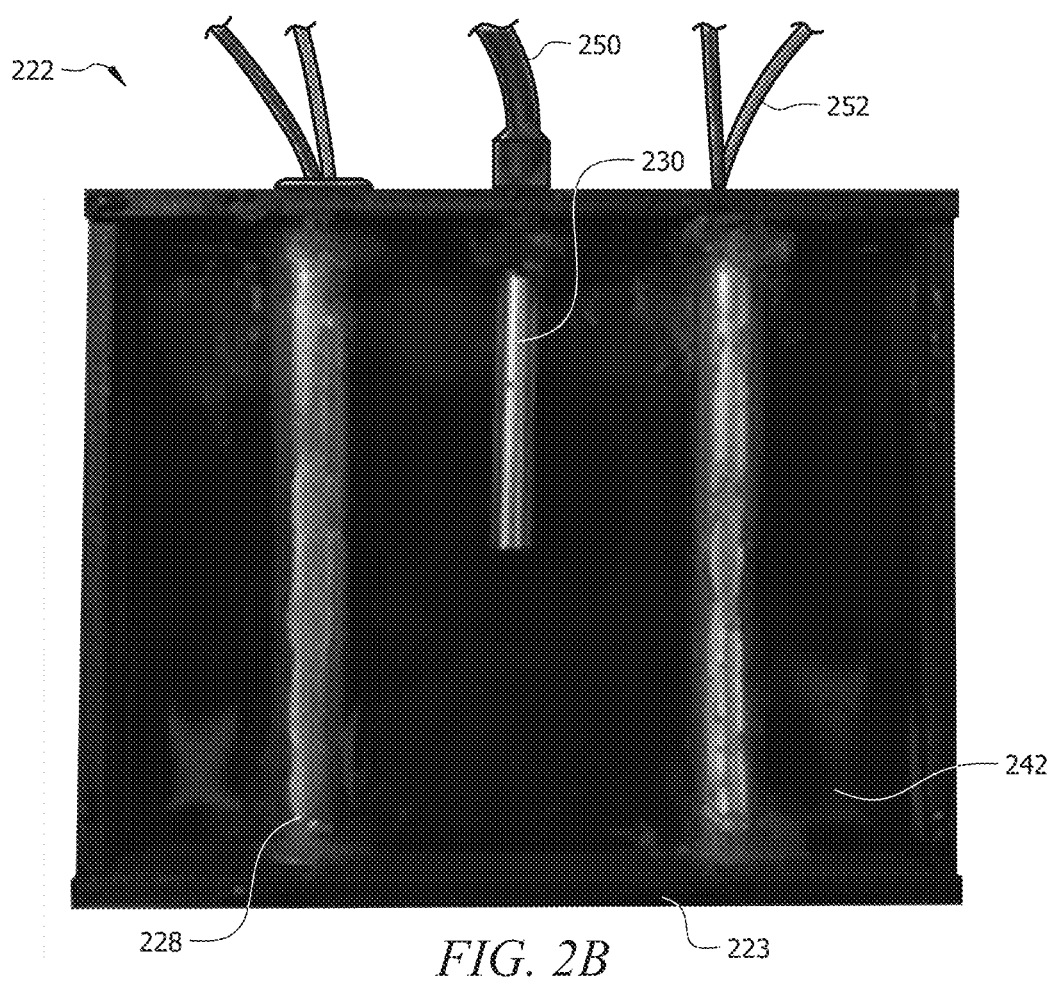

The first step of ELISA is antibody conjugation with the target protein performed at 37° C., therefore a system for portable ELISA should include an incubator that can accurately maintain the needed temperature. For uniform heating of the ELISA microwells, a water bath 222 and a waterproof temperature probe 230 are used. The water bath 222 includes two copper tubes 228 integrated with heating elements 252, and the waterproof temperature probe 230 was used for continuous temperature monitoring via wire 250 (FIGS. 2A-2D). The top view of the whole water bath 222 heater in operation is shown in FIGS. 2A-2B. The thermal image (FIG. 2A), taken with an FLIR camera, demonstrates that the temperature 260 is the highest around the heaters, but is rather uniform between the heaters. The inside 242 of the water bath 222 is surrounded by water bath edge 223. The thermal image FIG. 2A shows variations in temperature by gradient 262.

Figure 2C:
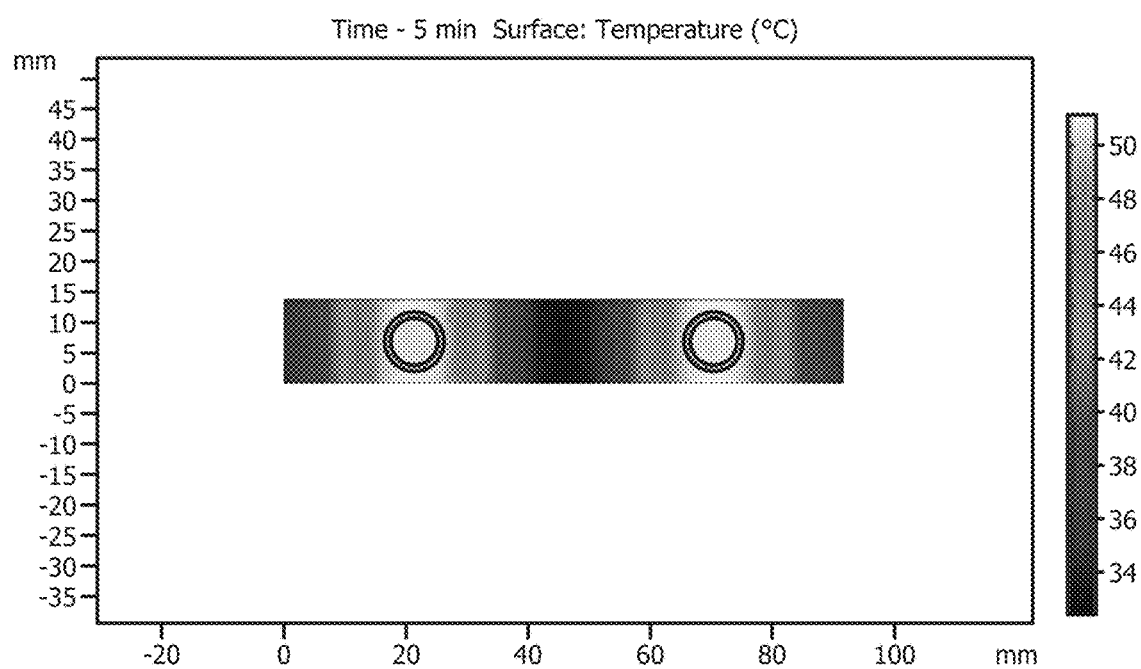
Figure 2D:
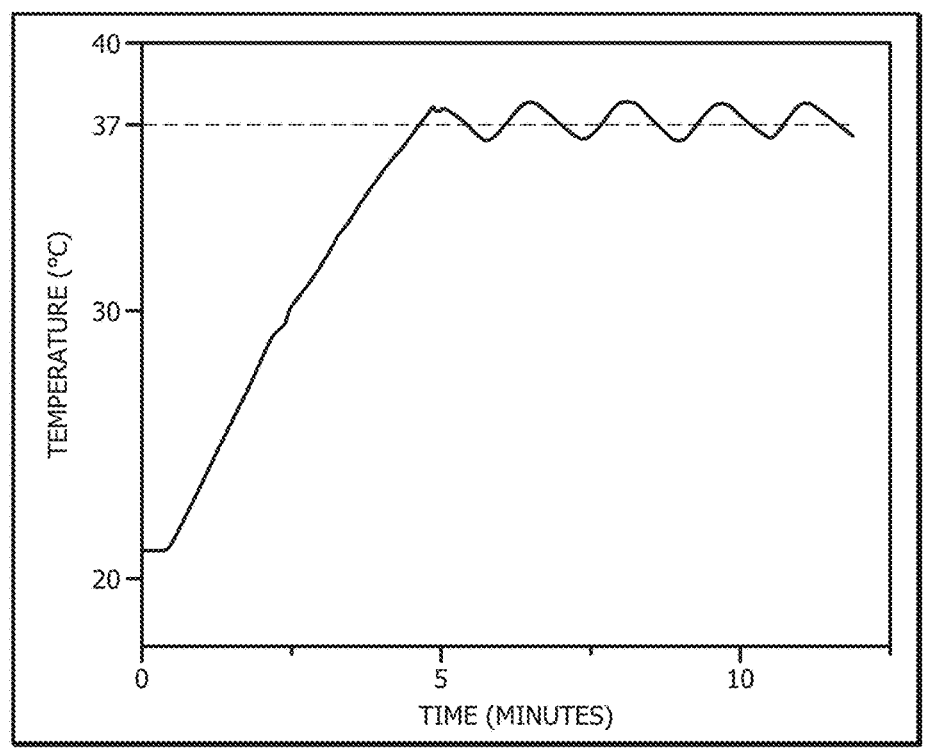

A cross-sectional COMSOL simulation of the heating system is shown in FIG. 2C, demonstrating the uniform heat propagation across the water layer. The ELISA microwells are placed in two rows alongside the heaters to ensure identical thermal treatment of all the samples. Since most ELISA reactions take place at 37° C., accurate control of the heaters is necessary to maintain this temperature. The heaters are controlled through solid state relays by an Arduino Mega 2560 microcontroller. When the temperature probe reads less than 37° C., the relays are enabled, which powers the heating elements. When the temperature is greater than 37° C., the relay closes, switching the heaters off. The ELISA microwells are placed in holders, with their outside surfaces contacting the warm water in order to provide the temperature necessary for the conjugation reactions to occur. The water bath and the slower heat dissipation through the copper tubes help to prevent larger temperature fluctuations in the ELISA microwells. As shown in FIG. 2D, the water bath requires 5 minutes to reach the setpoint of 37° C. from ambient conditions. After reaching the setpoint, the temperature fluctuates within ±0.8° C. for the duration of incubation (about 60 minutes). This precision is sufficient for reproducible ELISA measurements (17OH Progesterone ELISA for Routine Analysis, 2012).

Optical Readout Design

The next ELISA step after completing the incubation, is adding a secondary colorimetric antibody followed by quantifying the sample absorption with a plate reader. As a substitute for a plater reader, MELISA uses a smartphone camera and this data is then compared with data obtained using a commercial plate reader. To remove interference from the ambient light while taking an image with a mobile phone camera, the samples are placed inside of a black box similar to Chroma-dock (Konnaiyan and Pyayt, 2015). As a light source, a white LCD screen can be placed under the samples, and it produced uniform illumination. The camera from the mobile phone was used for the colorimetric measurements, and during the measurements camera parameters such as white balance, ISO, and exposure rate were fixed (Hirsch, 2013).

Operation

Figure 3A:
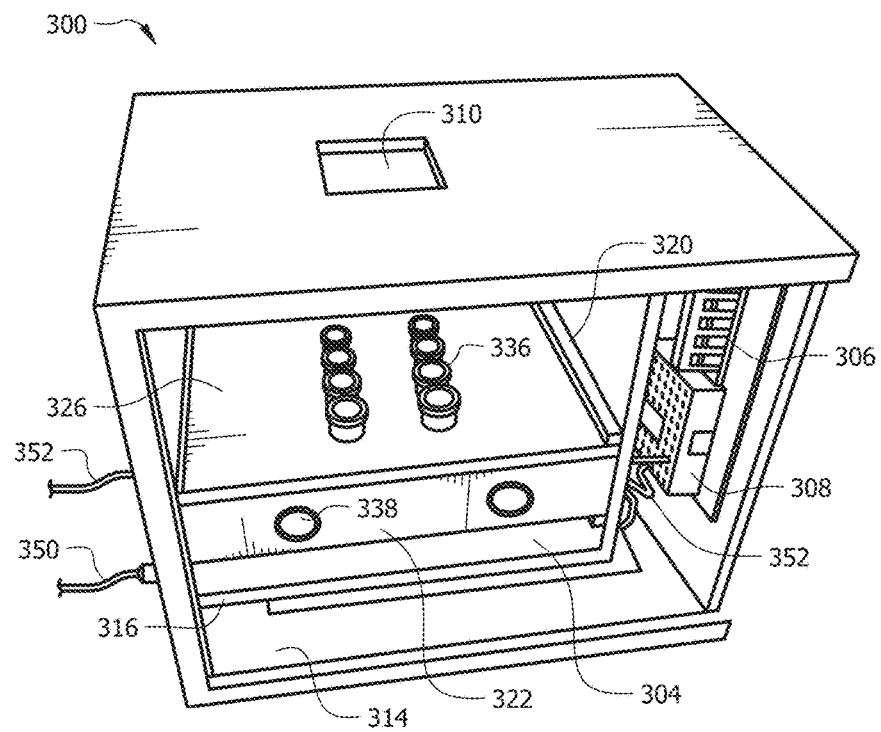
FIGS. 3A-3D depict demonstration of an embodiment of the claimed subject matter. 3A: Sample incubation mode; 3B: Loading image capturing tray; 3C: Image capturing mode; 3D: Captured sample image (colored dyes for demonstration).

The first step in the ELISA procedure is shown in FIG. 3A. The housing 300 is comprised of an inner chamber 316 and outer chamber 314. The top of the housing 300 contains an aperture 310 leading into the inner chamber 316. At this stage the water bath 322 has been place into the inner chamber using rail 320 to guide and secure the water bath 322 in place. The copper tube ends 338 protrude out of the water bath 322. The heating tray 326 contains microwells 336 used for ELISA incubation. Under the water bath 322 is the light source 304. The heating units and temperature probes are controlled via wires 350 and 352. The control circuitry 306 and DC solid state relays 308 are linked to the heating elements and probes via wires 352.

Figure 3B:
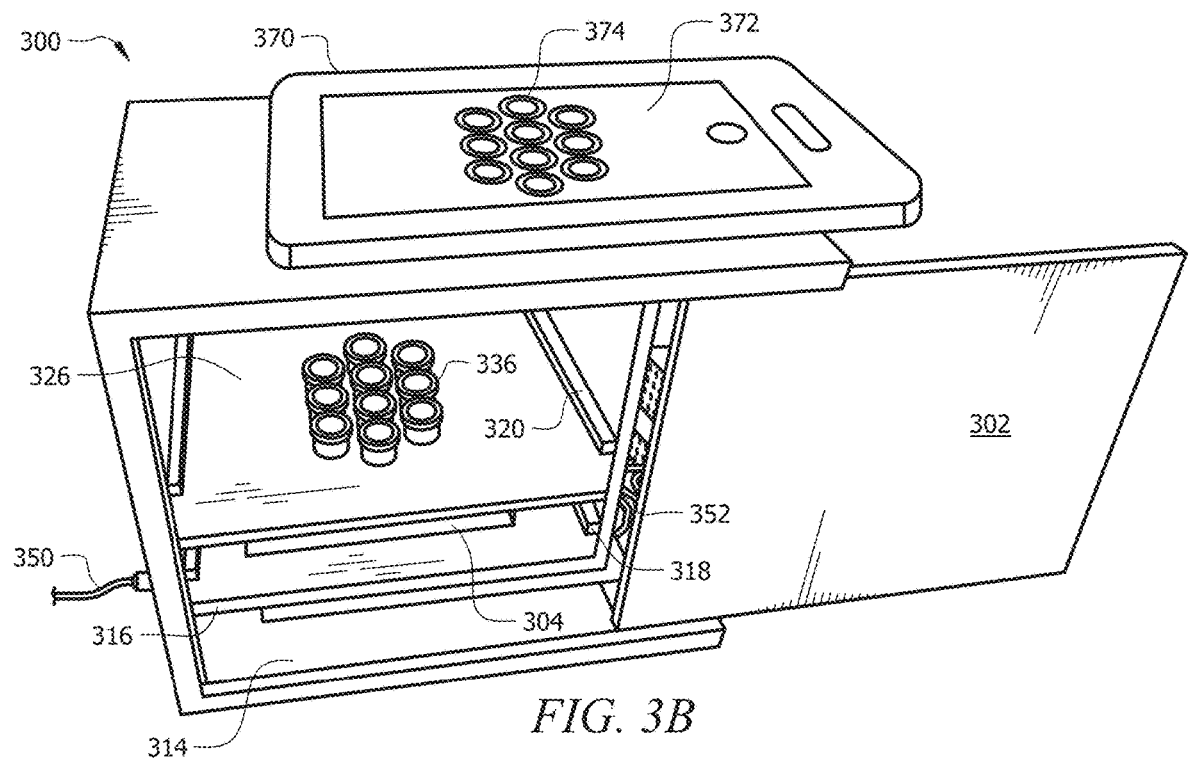

In one embodiment, progesterone samples are added to the microwells and inserted into the sample holder under controlled temperature environment in the water bath. After heating the samples to 37° C. and maintaining this temperature for 60 minutes, the microwells are removed from the water bath and placed into the viewing tray 326, which is then placed on the same rails 320 used for the bath, as shown in FIG. 3B.

Figure 3C:
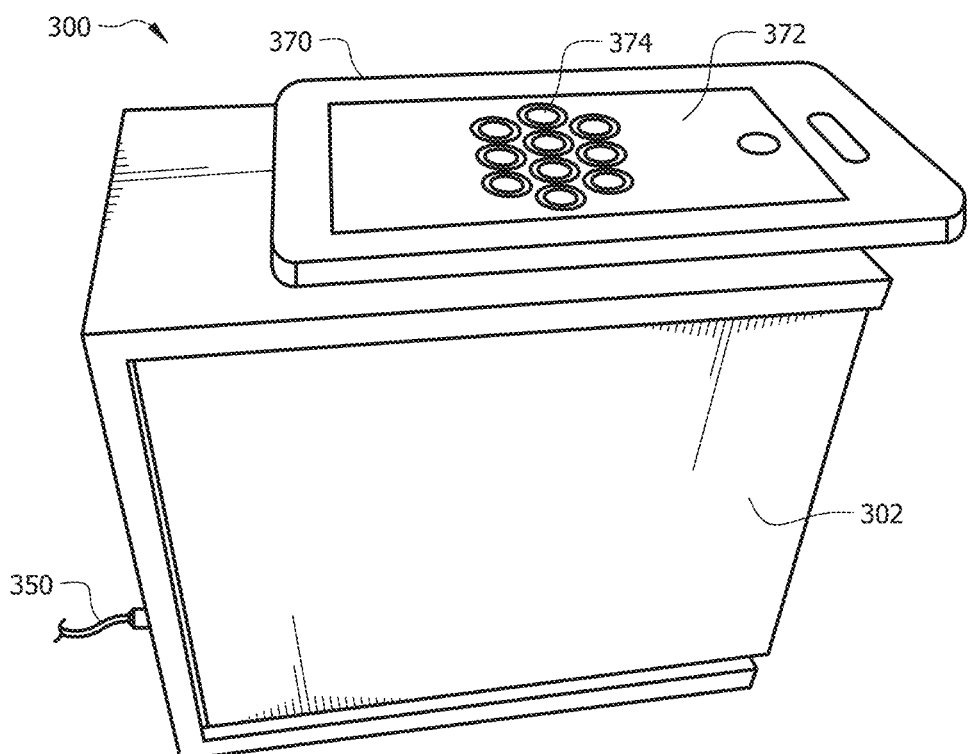
Figure 3D:
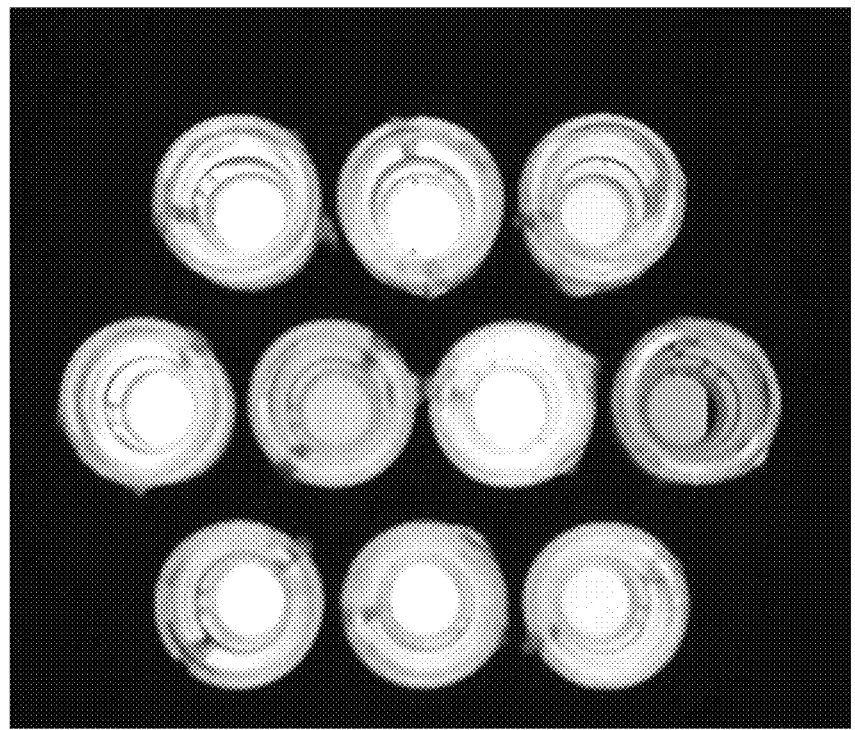

Once the microwell-loaded viewing tray 326 has been placed inside the MELISA device, the door 302 is closed, and the LCD screen 304 located below the viewing tray emits light through the bottom of the microwells 336. In order to capture the images of the samples, a smartphone or mobile device 370 is placed on top of the MELISA housing 300, and the camera aperture is aligned with the square-inch hole 310, with this step shown in FIG. 3C. The mobile device 370 has a display 372 which depicts the microwell color image 374. With all ambient light blocked by both the door 302 and the enclosed design of the box, color contrast is more discernable, focus is improved, and the overall image quality is enhanced. After loading the viewing tray 326 into the housing and closing the door 302, the color concentrations of the ELISA samples can be recorded with a smartphone 370. An example of the resulting image captured by a smartphone is shown in FIG. 3D.

It can be understood that the foregoing steps do not need to take place in any particular order, other than first heating the samples to a predetermined temperature and subsequently capturing images of those samples. For example, there may be differing rails for each of the trays and the light source, so that they do not have to be removed and replaced as often. Additionally, the heating tray and the image capturing tray may be the same tray but used in holding the microwells both during heating and during image capture. Further, the light source may be positioned within the housing at all times but simply powered on and off as needed. Differing configurations and methodologies are contemplated herein.

Example 1—Evaluation of MELISA

The next step was evaluation of MELISA using actual ELISA measurements. One of the hormones vital to female reproduction health is progesterone, which regulates a number of critical physiological processes, affecting blood pressure and the cardiovascular system in general (Barbagallo et al., 2001). In addition, progesterone significantly influences the ability to conceive and has a major impact on pregnancy overall (Xu et al., 2012; Csapo et al., 1974). Progesterone has a big role in maintaining a healthy immune system and influences development of neoplastic diseases (Stopińska-Gluszak et al., 2006). Healthy ranges of progesterone concentrations for women in the follicular phase is 0.2 ng/ml-1.3 ng/ml, 1.0 ng/ml-4.5 ng/ml in the luteinic phase, and 0.2 ng/ml-0.9 ng/ml in menopause (17OH Progesterone ELISA for Routine Analysis, 2012). Low levels of progesterone may increase the risk of endometrial and breast cancer (Kim et al., 2013). In addition to ELISA, progesterone levels can also be measured by protein-binding techniques (Yoshimi and Lipsett, 1968), radio-immunoassays (Abraham et al., 1971), and liquid chromatography—tandem mass spectrometry (Inder et al., 2012). These other methods are not designed for point-of-care or at-home use due to the need for specialized equipment and high cost.

To test the MELISA design, a 17OH progesterone ELISA kit (17OH Progesterone ELISA for Routine Analysis, 2012; Elder et al., 1987) was used and results from the measurements were compared with the measurements conducted using current gold standard instrument, a Fisher Scientific AccuScan plate reader. The ELISA kit contains antibody-coated microplates, calibration samples, and a substrate required for quantitative determination of progesterone concentration. Calibration samples have progesterone concentrations of 0, 0.2, 0.4, 1.6, 6.4, and 19.2 ng/mL, respectively. After incubation and solid-phase washing, horseradish peroxidase (HRP), conjugated with 17OH antigens, binds to anti-17OH progesterone antibodies. The HRP-antibody binding, along with the addition of $H_2O_2$-tetramethylbenzidine ($H_2O_2$-TMB) and a sulfuric acid stop solution, resulting in a color change. The ELISA samples' color intensity is inversely proportional to 17OH progesterone hormone concentration. The final step is to measure sample absorption using the current gold standard to validate results.

Procedure

Blood samples were purchased from Innovative Research and a 17OH ELISA calibration kit was used to measure progesterone concentration in blood plasma with the MELISA device. The blood samples were allowed to sediment, with 50 μL of plasma collected from the top layer of each sample, and dispensed into each sample microwell. After six calibration samples and three unknown samples were loaded in the heating tray, samples were incubated for 60 minutes at 37° C. After incubation, the contents of the microwells were washed out with deionized (DI) water and moved to an image capturing tray. 100 μl of H2O2-Tetramethylbenzidine ($H_2O_2$-TMB) (0.26 g/L concentration) is added to each sample binding to the 17OH antigens are conjugated with HRP chromogenic agent, to initiate the binding of a chromogenic agent to the ELISA antibodies. The image capturing tray is then placed back in the enclosure at ambient temperature with the door closed. After 15 minutes in the dark, (0.15 mol/L concentration) stop solution is added to the samples which prepares them for optical reading (17OH Progesterone ELISA for Routine Analysis, 2012).

Figure 4:
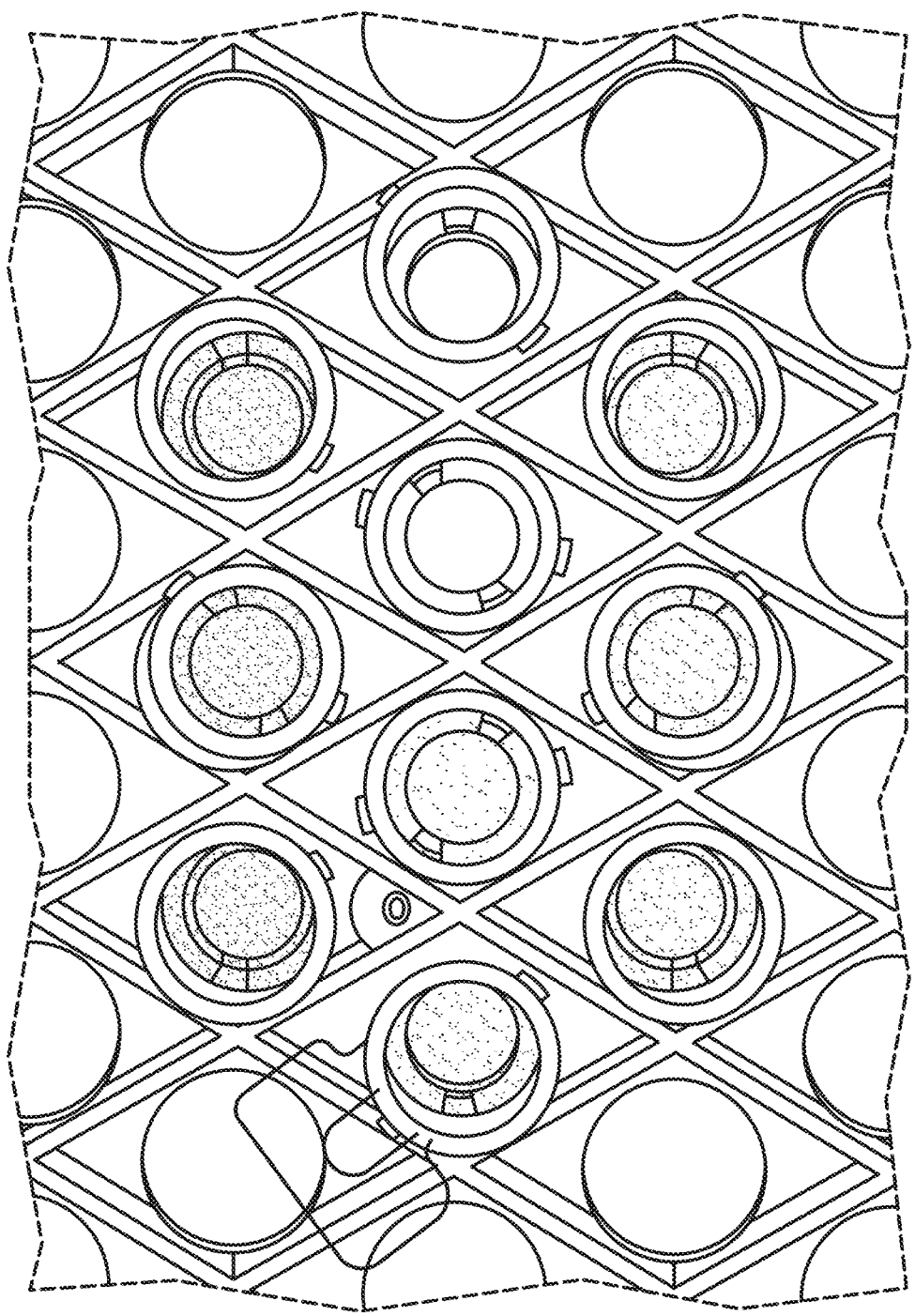
FIG. 4 is an image of progesterone ELISA samples: (1) 0 ng/ml, (2) 0.2 ng/ml, (3) 0.4 ng/ml, (4) 1.6 ng/ml, (5) 6.4 ng/ml, (6) 19.2 ng/ml, (7) blank, (8-10) unknown concentration.

An image of the samples was captured inside the system with the backlight LCD as shown in the FIG. 4. The white balance setting of the camera was used to adjust the color of the captured image based on the light source. The main advantage of using an automatic white balance setting is the color reproducibility for images captured under different light conditions (Hsu et al., 2008). Since a stable light source was used as a background in the experimental setup, the white balance was set to a 'daylight' mode, which normalizes the color values based on the standard daylight illuminant source D65. The autofocus option in a camera can cause blur in images that can add error to the measurements (Brown, 2000). Fixed focus mode was programmed into the mobile application as the distance between the object and the camera is constant, which is determined by the height of the box.

B. Data Analysis

Figure 5:
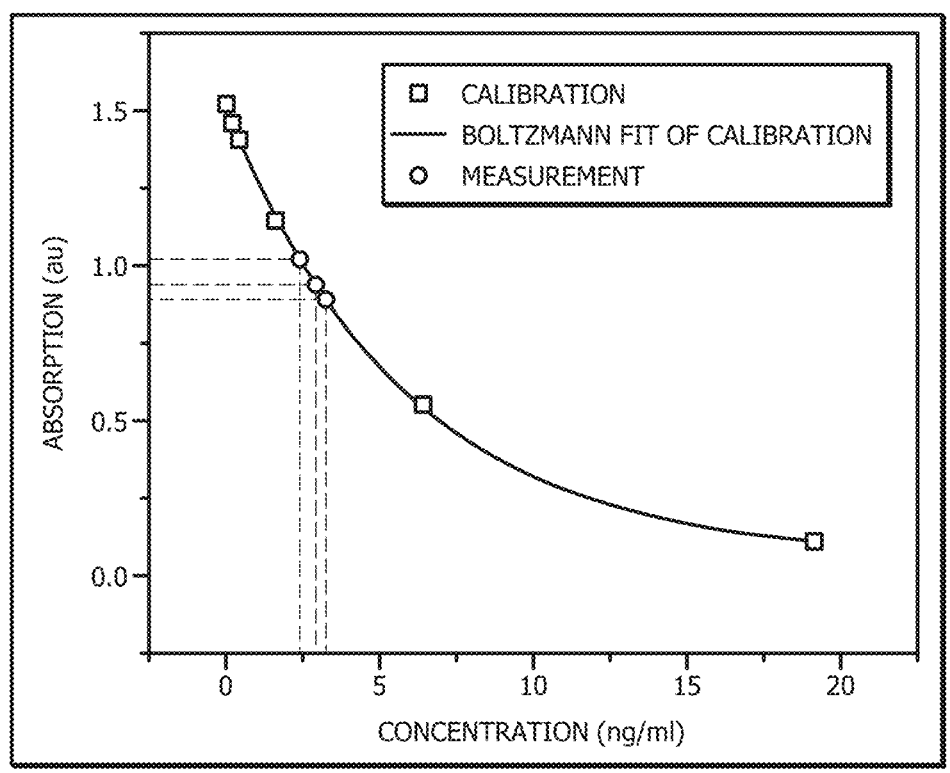
FIG. 5 is a plate reader progesterone concentration calibration curve.

The conventional measurement of progesterone concentrations of the ELISA samples was performed using a commercially available Fisher Scientific AccuScan microplate reader. Monochromatic light with 450 nm wavelength was used by the reader to measure the absorbance of the calibration samples, and they were plotted against their respective concentrations (FIG. 5). An Origin software package was used to fit the data points with a four-parameter Boltzmann Sigmoid function (Cheemalapati et al., 2016) (1):

$$y = A_2 + \left( \frac{A_1 - A_2}{1 + e^{\frac{x-x_0}{dx}}} \right) \quad (1)$$

where $x_0$ is the center of the Sigmoid; dx is the span of the curve; $A_1$ and $A_2$ are the minimum and the maximum values of the curve. The calibration curve obtained using the calibration samples can be used to measure the concentration of unknown samples based on the absorbance value.

Figure 6:
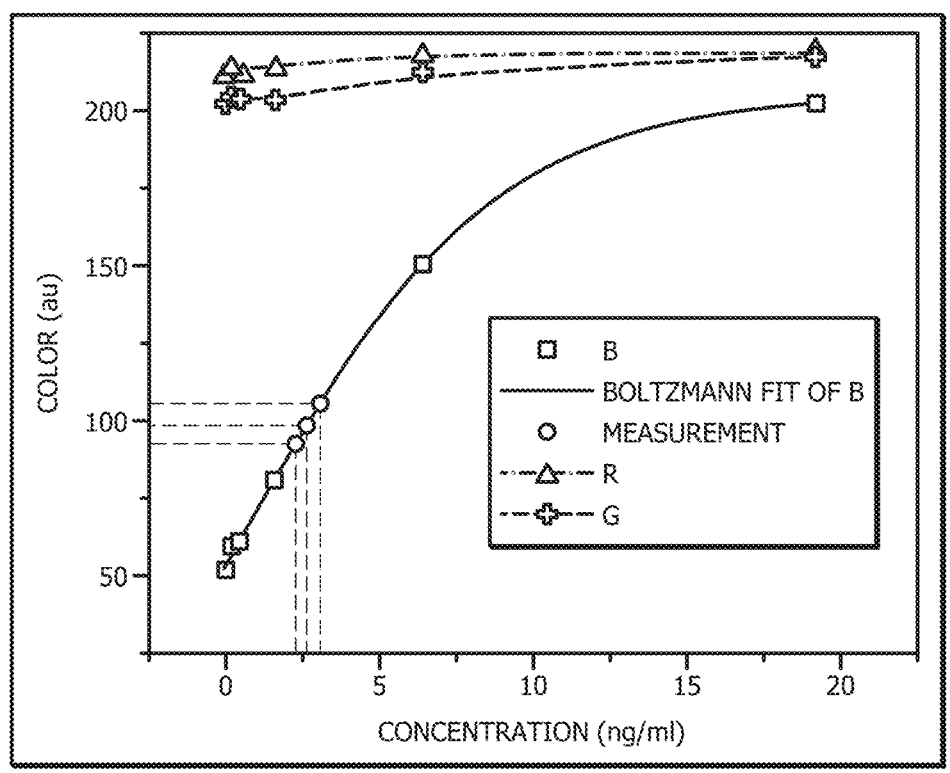
FIG. 6 is a MELISA progesterone concentration calibration curve.
Figure 7:
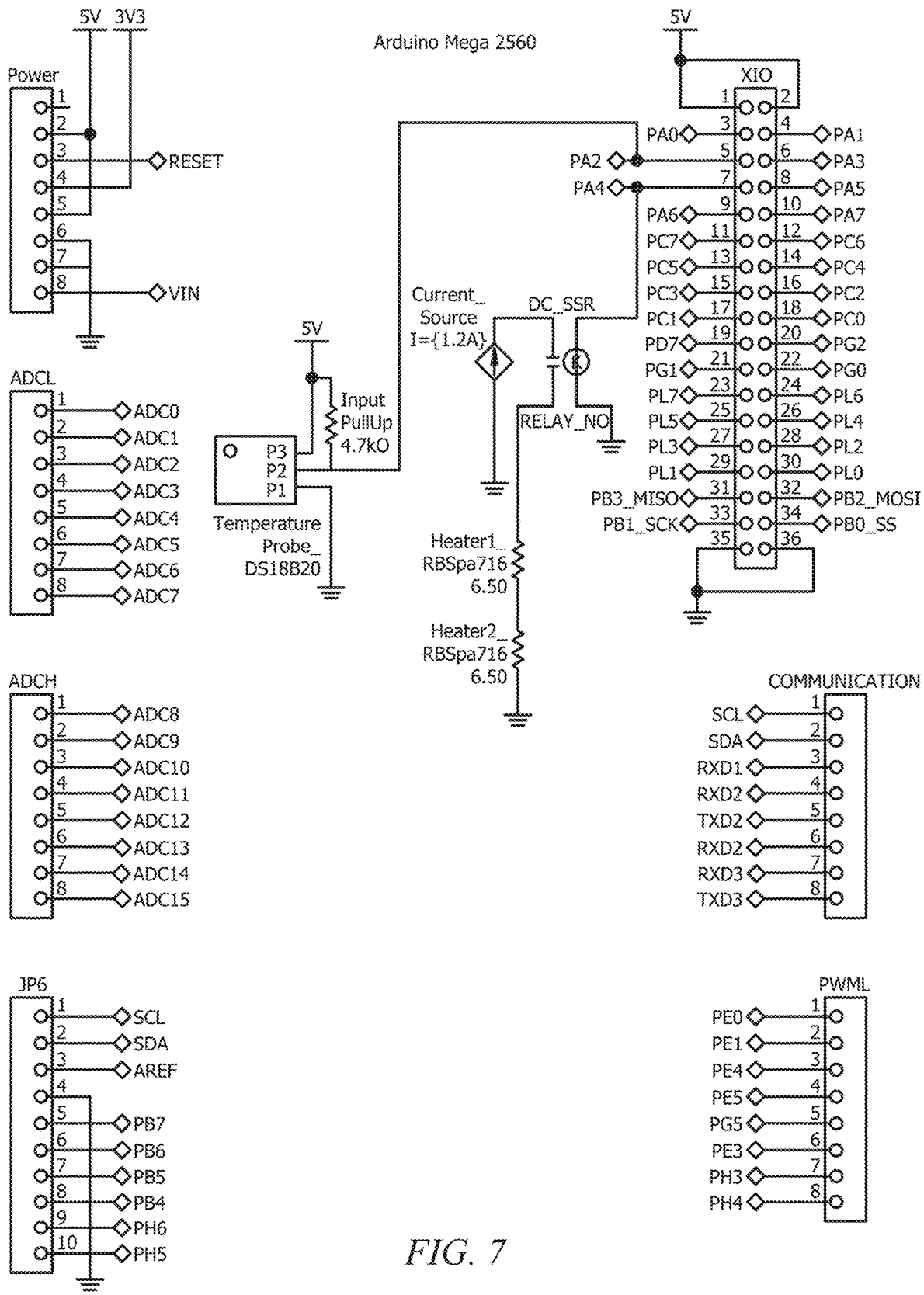
FIG. 7 is a circuit diagram used for certain embodiments of the current invention.

In the captured image, samples 1-6 are known progesterone values used for calibration, while samples 8-10 are unknown. RGB values of the calibration samples were measured and plotted against respective concentrations (FIG. 6). The red (R) and green (G) values are insignificant due to the low range of measured values. The blue (B) component has the range required to construct the calibration curve using the four-parameter Boltzmann Sigmoid function (1). Applying the calibration function to the B values of the unknown samples was used to determine the concentration.

The results of measuring the progesterone concentrations of the unknown samples with the commercially available plate reader and with MELISA are shown in Table 1. Comparing the values from the two measurements shows the accuracy of the MELISA system is within 10% of the gold standard. This is within value variability of the ELISA kit.

TABLE 1

Unknown samples calculated values

| Sample number | Plate reader measured concentration (ng/ml) | System measured concentration (ng/ml) |
|---|---|---|
| 8 | 2.9 | 2.6 |
| 9 | 2.39 | 2.24 |
| 10 | 3.23 | 3.04 |

In conclusion, a mobile ELISA (MELISA) system was evaluated herein for point of care measurements of progesterone concentration. Multiple samples with known concentrations of progesterone were analyzed using the MELISA system and accuracy was verified using a gold standard plate reader (Fisher Scientific AccuScan). The device consists of a dual-purpose enclosure used for incubation and image capturing of ELISA samples. A water bath heater was used to incubate samples at a target temperature, and then images were captured using a mobile phone and analyzed to measure progesterone concentrations. Adobe Photoshop was used to determine the RGB color components of each sample. The blue color component was used for further analysis due to its sensitivity to the changes in progesterone concentration. It was shown that progesterone ELISA samples can be incubated and measured, color values extracted, data analyzed, and a calibration curve built based on the blue component of RGB data. A close correlation between mobile system measurements and the data from the plate reader was demonstrated. Finally, it was shown that the results acquired with the current system matched the gold standard plate reader within 10%.

Example 2—Hardware and Software Infrastructure

The present invention may be embodied on various computing platforms that perform actions responsive to software-based instructions and most particularly on touchscreen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

REFERENCES

17OH Progesterone ELISA for Routine Analysis, 2012. 17OH Progesterone ELISA for Routine Analysis (pamphlet).

Abraham, G. E., Hopper, K., Tulchinsky, D., Swerdloff, R. S., Odell, W. D., 1971. Simultaneous Measurement of Plasma Progesterone, 17-Hydroxyprogesterone and Estradiol-17B by Radioimmunoassay. Analytical Letters 4, 325-335.

Archibong, E., Konnaiyan, K. R., Kaplan, H., Pyayt, A., 2017. A mobile phone-based approach to detection of hemolysis. Biosensors and Bioelectronics 88, 204-209.

Barbagallo, M., Dominguez, L. J., Licata, G., Shan, J., Bing, L., Karpinski, E., Pang, P. K. T., Resnick, L. M., 2001. Vascular Effects of Progesterone: Role of Cellular Calcium Regulation. Hypertension 37, 142-147.

Brown, G., 2000. How Autofocus Cameras Work [WWW Document]. HowStuffWorks.

Catalani, C., Philbrick, W., Fraser, H., Mechael, P., Israelski, D. M., 2013. mHealth for HIV Treatment & Prevention: A Systematic Review of the Literature. The Open AIDS Journal 7, 17-41.

Cheemalapati, S., Ladanov, M., Pang, B., Yuan, Y., Koria, P., Xia, Y., Pyayt, A., 2016. Dynamic visualization of photothermal heating by gold nanocages using thermoresponsive elastin like polypeptides. Nanoscale 8, 18912-18920.

Cheng, C., Brown, R. C., Cohen, L. L., Venugopalan, J., Stokes, T. H., Wang, M. D., 2013. iACT—An interactive mHealth monitoring system to enhance psychotherapy for adolescents with sickle cell disease. 2013 35th Annual International Conference of the IEEE Engineering in Medicine and Biology Society (EMBC).

Csapo, A. I., Pohanka, O., Kaihola, H. L., 1974. Progesterone Deficiency and Premature Labour. Bmj 1, 137-140.

Elder, P., Yeo, K., Lewis, J., Clifford, J., 1987. An enzyme-linked immunosorbent assay (ELISA) for plasma progesterone: immobilised antigen approach. Clinica Chimica Acta 162, 199-206.

Hirsch, R., 2013, Exploring Color Photography Fifth Edition: From Film to Pixels. Taylor & Francis.

Hsu, E., Mertens, T., Paris, S., Avidan, S., Durand, F., 2008. Light mixture estimation for spatially varying white balance. ACM SIGGRAPH 2008 papers on —SIGGRAPH 08.

Inder, W. J., Dimeski, G., Russell, A., 2012. Measurement of salivary cortisol in 2012—laboratory techniques and clinical indications. Clinical Endocrinology 77, 645-651.

Jenkins, C., Burkett, N.-S., Ovbiagele, B., Mueller, M., Patel, S., Brunner-Jackson, B., Saulson, R., Treiber, F., 2016. Stroke patients and their attitudes toward mHealth monitoring to support blood pressure control and medication adherence. mHealth 2, 24-24.

Katz, R., Mesfin, T., Barr, K., 2012. Lessons From a Community-Based mHealth Diabetes Self-Management Program: "It's Not Just About the Cell Phone". Journal of Health Communication 17, 67-72.

Kim, J. J., Kurita, T., Bulun, S. E., 2013. Progesterone Action in Endometrial Cancer, Endometriosis, Uterine Fibroids, and Breast Cancer. Endocrine Reviews 34, 130-162.

Konnaiyan, K. R., Cheemalapati, S., Pyayt, A., Gubanov, M., 2016. mHealth dipstick analyzer for monitoring of pregnancy complications. 2016 IEEE Sensors.

Konnaiyan, K. R., Pyayt, A., 2015. Smartphone Based 3D Printed Colorimeter For Biomedical Applications (thesis).

McGeough, C. M., O'Driscoll, S., 2013. Camera Phone-Based Quantitative Analysis of C-Reactive Protein ELISA. IEEE Transactions on Biomedical Circuits and Systems 7, 655-659.

Stopińska-Gluszak, U., Waligóra, J., Grzela, T., Gluszak, M., Józwiak, J., Radomski, D., Roszkowski, P. I., Malejczyk, J., 2006. Effect of estrogen/progesterone hormone replacement therapy on natural killer cell cytotoxicity and immunoregulatory cytokine release by peripheral blood mononuclear cells of postmenopausal women. Journal of Reproductive Immunology 69, 65-75.

Turner-Mcgrievy, G. M., Beets, M. W., Moore, J. B., Kaczynski, A. T., Barr-Anderson, D. J., Tate, D. F., 2013. Comparison of traditional versus mobile app self-monitoring of physical activity and dietary intake among overweight adults participating in an mHealth weight loss program. Journal of the American Medical Informatics Association 20, 513-518.

Vashist, S. K., Oordt, T. V., Schneider, E. M., Zengerle, R., Stetten, F. V., Luong, J. H., 2015. A smartphone-based colorimetric reader for bioanalytical applications using the screen-based bottom illumination provided by gadgets. Biosensors and Bioelectronics 67, 248-255.

Xu, B., Li, Z., Zhang, H., Jin, L., Li, Y., Ai, J., Zhu, G., 2012. Serum progesterone level effects on the outcome of in vitro fertilization in patients with different ovarian response: an analysis of more than 10,000 cycles. Fertility and Sterility 97.

Yoshimi, T., Lipsett, M., 1968. The measurement of plasma progesterone. Steroids 11, 527-540.

Zangheri, M., Cevenini, L., Anfossi, L., Baggiani, C., Simoni, P., Nardo, F. D., Roda, A., 2015. A simple and compact smartphone accessory for quantitative chemiluminescence-based lateral flow immunoassay for salivary cortisol detection. Biosensors and Bioelectronics 64, 63-68.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. While the disclosure is susceptible to various modifications and implementation in alternative forms, specific embodiments have been shown by way of non-limiting example in the drawings and have been described in detail herein. Since certain changes may be made in the above construction without departing from the scope of the instant application, it is intended that all matters contained in the foregoing description or shown in the accompanying drawings shall be interpreted as illustrative and not in a limiting sense.

The disclosure is not intended to be limited to the particular forms disclosed.

Rather, the disclosure is to cover all modifications, equivalents, and alternatives falling within the scope of the disclosure as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

It is also to be understood that the following claims are intended to cover all of the generic and specific features of the invention herein described, and all statements of the scope of the invention that, as a matter of language, might be said to fall therebetween.

What is claimed is:

1. A device for incubating and measuring a concentration of a target binding domain in a biological sample from a subject comprising:
    a housing comprising a top, a bottom, a first side, a second side, a front, and a rear defining an interior space within wherein the interior space is divided into an inner chamber and an outer chamber;
    an aperture configured to receive a camera of a mobile device wherein the aperture is disposed on the top of the housing and opens to the inner chamber;
    a door disposed in the front of the housing and configured to move between an open configuration and a closed configuration, wherein the closed configuration minimizes external light entering the housing;
    a thermally conductive sample holder removably positioned within the inner chamber wherein the thermally conductive sample holder comprises a sample holder tray and at least one heating element within a water bath;
    wherein the sample holder tray has a plurality of apertures for receiving a plurality of enzyme-linked immunosorbent assay (ELISA) microwells, such that a portion of the plurality of the ELISA microwells are submerged partially within the water bath;
    a temperature sensor within the water bath for continuous temperature monitoring of the water bath;
    a light source positioned in the bottom of the inner chamber;
    a power source; and
    circuitry and relays for controlling a temperature of the water bath wherein the circuitry and relays are disposed in the outer chamber.

2. The device of claim 1, wherein the mobile device camera acquires color images of contents of the ELISA microwells.

3. The device of claim 2, wherein the mobile device contains software configured to analyze the color images acquired by the mobile phone camera to correlate color intensity of a selected portion of the color images with a target binding domain concentration using a baseline curve calculation.

4. The device of claim 1, further comprising a removable image capture tray positioned in the inner chamber above the light source when the thermally conductive sample holder is removed from the inner chamber.

5. The device of claim 4, wherein the removable image capture tray has a plurality of apertures for receiving the ELISA microwells.

6. The device of claim 5, wherein the plurality of apertures of the removable image capture tray are arranged in a hexagonal pattern for optimal light distribution.

7. The device of claim 1, wherein the plurality of apertures in the sample holder tray are arranged to be equidistant from the at least one heating element in the water bath to ensure uniform heating.

8. A method for incubating and analyzing a target binding domain in a biological sample, the method comprising:
    providing a biological sample from a subject;
    providing a thermally conductive sample holder comprising a sample holder tray and a water bath having at least one heating element and a temperature sensor;

loading the biological sample into the sample holder tray wherein the sample holder tray comprises a plurality of apertures holding enzyme-linked immunosorbent assay (ELISA) microwells;

positioning the sample holder tray in the water bath such that a portion of the plurality of ELISA microwells containing the sample are partially submerged in the water bath;

inserting the thermally conductive sample holder into a device for incubating and measuring a concentration of a target binding domain in the biological sample wherein the device comprises a housing having a top, a bottom, a first side, a second side, a front, and a rear defining an interior space within wherein the interior space is divided into an inner chamber and an outer chamber;

an aperture disposed on the top of the housing wherein the aperture opens to the inner chamber and is configured to receive a mobile device having a camera;

a door disposed in the front of the housing and configured to move between an open configuration and a closed configuration, wherein the closed configuration minimizes external light entering the housing;

a light source positioned in the bottom of the inner chamber;

a power source; and circuitry and relays disposed in the outer chamber for controlling a temperature of the water bath;

incubating the biological sample contained in the ELISA microwells in the device with continuous temperature monitoring;

removing the water bath from the inner chamber;

adding reagents to the ELISA microwells for performing a colorimetric portion of the ELISA in the device;

using the light source to illuminate the ELISA microwells with the door in the closed configuration to minimize the external light entering the housing;

generating a color image of the biological sample contained in the ELISA microwells using a mobile device having a camera positioned over the aperture on the top of the housing;

determining color intensity of a selected portion of the color image; and correlating the color intensity of the selected portion of the color image with a target binding domain concentration using a baseline curve calculation.

9. The method of claim 8, further comprising removing the ELISA microwells from the sample holder tray after the incubation and placing the ELISA microwells into an image capture tray having a plurality of apertures.

10. The method of claim 9, wherein the plurality of apertures of the image capture tray are arranged in a hexagonal pattern for optimal light distribution.

11. The method of claim 8, wherein the plurality of apertures in the sample holder tray are arranged to be equidistant from the at least one heating element in the water bath to ensure uniform heating.

12. The method of claim 8, further comprising reporting the concentration of the target binding domain on the mobile device and comparing the reported concentration of the target binding domain to a threshold concentration to determine presence or absence of a pathological condition.

13. A system for performing an enzyme-linked immunosorbent assay (ELISA) comprising:

a device for performing the ELISA comprising a housing comprising a top, a bottom, a first side, a second side, a front, and a rear defining an interior space within wherein the interior space is divided into an inner chamber and an outer chamber;

an aperture configured to receive a camera of a mobile device wherein the aperture is disposed on the top of the housing wherein the aperture opens to the inner chamber;

a door disposed in the front of the housing configured to move between an open configuration and a closed configuration, wherein the closed configuration minimizes external light entering the housing;

a thermally conductive sample holder disposed within the inner chamber wherein the thermally conductive holder comprises a sample holder tray and at least one heating element within a water bath;

wherein the sample holder tray has a plurality of apertures for receiving a plurality of ELISA microwells, such that a portion of the plurality of the ELISA microwells are submerged partially within the water bath;

a temperature sensor within the water bath for continuous temperature monitoring of the water bath;

a light source positioned in the bottom of the inner chamber;

a power source; and circuitry and relays for controlling the temperature of the water bath wherein the circuitry and relays are disposed in the outer chamber; and a mobile device having a camera and containing software configured to analyze colorimetric data generated by the ELISA.

14. The system of claim 13, further comprising a removable image capture tray positioned in the inner chamber above the light source when the thermally conductive sample holder is removed from the inner chamber.

15. The system of claim 14, wherein the removable image capture tray has a plurality of apertures for receiving the ELISA microwells.

16. The system of claim 15, wherein the plurality of apertures of the removable image capture tray are arranged in a hexagonal pattern for optimal light distribution.

17. The system of claim 13, wherein the plurality of apertures in the sample holder tray are arranged to be equidistant from the at least one heating element in the water bath to ensure uniform heating.

* * * * *